United States Patent [19]

Tancrell

[11] 4,145,931
[45] Mar. 27, 1979

[54] FRESNEL FOCUSSED IMAGING SYSTEM

[75] Inventor: Roger H. Tancrell, Cambridge, Mass.

[73] Assignee: Raytheon Company, Lexington, Mass.

[21] Appl. No.: 866,325

[22] Filed: Jan. 3, 1978

[51] Int. Cl.² .......................................... G01N 29/00
[52] U.S. Cl. .................................. 73/626; 128/2 V
[58] Field of Search ............... 73/626, 610, 612, 613, 73/618; 340/1 R, 3 R, 5 R, 9; 128/2 V, 2.052

[56] References Cited

U.S. PATENT DOCUMENTS

| | | | |
|---|---|---|---|
| 3,504,368 | 3/1970 | Ruben | 343/701 |
| 3,805,596 | 4/1974 | Klahr | 73/626 |
| 3,911,730 | 10/1975 | Niklas | 73/626 |
| 3,919,683 | 11/1975 | Itamura et al. | 73/626 |
| 4,080,838 | 3/1978 | Kuroda et al. | 73/612 |

OTHER PUBLICATIONS

P. Alais et al.; "Fresnel Zone Focusing of Linear Arrays Applied to B and C Echography;" Acoustica Holography, vol. 7, pp. 509–522, 8–1976.

*Primary Examiner*—Stephen A. Kreitman
*Attorney, Agent, or Firm*—David M. Warren; Joseph D. Pannone; Milton D. Bartlett

[57] ABSTRACT

An imaging system, particularly useful for acoustic medical diagnosis of a human subject, utilizes an array of radiating elements or sonic transducers located side-by-side and positioned along the subject. Signals received by the transducer are applied to a pair of pattern generation circuits which weight the individual signals by factors of +1, −1 or 0. Graphs of the weighting factors as a function of transducer location have the likeness of cosinusoidal and sinusoidal Fresnel patterns, these patterns being produced by the two circuits. The weighted signals of each pattern are summed together, multiplied by cosinusoidal and sinusoidal reference signals and then summed together to provide a radiation pattern which converges from the array to a focal point in front of the array while eliminating a diverging pattern from a virtual focus behind the array.

2 Claims, 9 Drawing Figures

FIG. 8

FRESNEL FOCUSSED IMAGING SYSTEM

BACKGROUND OF THE INVENTION

This invention relates to an imaging system employing an array of radiation detectors and, more particularly, the use of a Fresnel pattern impressed upon signals received by the detectors to provide for imaging as in the case of the sonic imaging of a human subject.

Fresnel masking has been utilized in both electromagnetic and sonic imaging systems. With respect to electromagnetic imaging systems, a Fresnel pattern is disclosed in the U.S. Pat. No. 3,263,079 which issued to L. N. Mertz and N. O. Young on July 26, 1966 wherein the pattern is utilized for forming the image of stars in the sky. The use of a Fresnel pattern in nuclear medicine for forming an image of a radioactive source is disclosed in the U.S. Pat. No. 3,936,639 which issued in the name of H. H. Barrett on Feb. 3, 1976. The use of a Fresnel pattern impressed upon the signals of sonic radiation detectors is disclosed in the U.S. Pat. No. 3,911,730 which issued in the name of L. Niklas on Oct. 14, 1975 wherein the energization of groups of radiation detectors, or transducers, is employed following the arrangement of a Fresnel pattern in at least one dimension. The use of an ultrasonic imaging scanner for imaging organs of the human body is disclosed in the U.S. Pat. No. 3,805,596 which issued in the name of C. N. Klahr on Apr. 23, 1974.

The use of the Fresnel pattern for sonic imaging systems is advantageous in that the Fresnel pattern provides for the focussing of the sonic radiation in the manner of a lens. A problem arises in that with systems of the prior art, the Fresnel patterns, whether it be utilized with a one dimensional line array or in a two dimensional array, produces the effect of both a converging pattern of radiation which converges toward a focal point in the subject in front of the array as well as a diverging radiation pattern which emanates from a virtual focus located behind the array. The energy content of signals produced by the transducers in response to incident sonic energy from the diverging radiation pattern approximately equals that of the energy content of signals associated with the desired converging pattern. As a result, there is substantial unwanted noise which degrades an image of the subject obtained with the converging radiation pattern.

SUMMARY OF THE INVENTION

The aforementioned problem is overcome and other advantages are provided by an imaging system in conjunction with radiating elements such as sonic transducers wherein, in accordance with the invention, a pair of Fresnel patterns are impressed upon signals of the transducers, one Fresnel pattern being a cosinusoidal Fresnel pattern while the second is a sinusoidal Fresnel pattern, for combining signals of the two patterns to produce a resultant radiation pattern of the array wherein the aforementioned undesirable diverging pattern is absent. Thereby, upon imaging a subject, such as a human being, various sites within the subject are viewed by the converging radiation pattern to produce a sharp image of each site without the interference associated with noise from the diverging radiation pattern. The imaging system of the invention is equally applicable to an array of detectors of electromagnetic radiation as well as to an array of detectors of sonic radiation. However, for convenience in describing the invention, reference will be made to sonic transducers, it being understood that the description is equally applicable to the case of electromagnetic radiation.

Each of the aforementioned Fresnel patterns is impressed upon signals produced by the transducers in response to sound waves incident thereupon by a set of multipliers which are coupled to individual ones of the transducers. Each multiplier multiplies the polarity of a transducer signal by a factor of $+1$, $-1$ or 0. In a preferred embodiment of the invention, each of the multipliers comprises an inverting amplifier with a selector switch which selects either the positive or negative output signals of the amplifier or provides for the grounding of the signal to provide the alternate value of 0. The multiplication factor for each transducer signal is selected in accordance with the location of the respective transducers within the array so that a graph of the multiplication factors, as a function of transducer location, has the appearance of a square wave approximation to a Fresnel pattern. A pair of the multipliers is coupled to each of the transducers so that the aforementioned pair of Fresnel patterns may be generated simultaneously.

The sum of the products of the multipliers for the cosinusoidal Fresnel patterns are then summed together and multiplied by a cosinusoidal reference signal. Similarly, the products of the multipliers for the sinusoidal Fresnel pattern are summed together and multiplied by a sinusoidal reference signal. The amplitudes of the products resulting from the multiplications with the two reference signals are then equalized and summed together. The resultant sum is then passed through a band pass filter to remove harmonics of the multiplication operation and then passed to a display whereby the various sites within the subject may be seen. A controller of the multiplying factors comprises a memory which is sequentially addressed in accordance with the range or depth within the subject or the respective sites for altering the Fresnel pattern for focussing at the respective sites whereby each of the sites is brought into sharp focus. At the conclusion of the displaying of sites along a normal to a group of transducers utilized in the Fresnel pattern, the multiplying factors are selected so as to shift the Fresnel pattern sideways along the array so as to focus on a contiguous portion of the subject. Continuous side-stepping of the Fresnel pattern permits the viewing of a swath or rectangular slice of the subject.

BRIEF DESCRIPTION OF THE DRAWINGS

The aforementioned aspects and other features of the invention are explained in the following description taken in connection with the accompanying drawings wherein:

FIG. 8 is a block diagram of a controller of the multiplying factors of FIG. 7, the controller including a memory storing the multiplication factors for the group of active transducers and a switching matrix for redirecting the factors as the group of active transducers is displaced sideways along the array for scanning the subject.

DESCRIPTION OF THE PREFERRED EMBODIMENT

Figure 1:
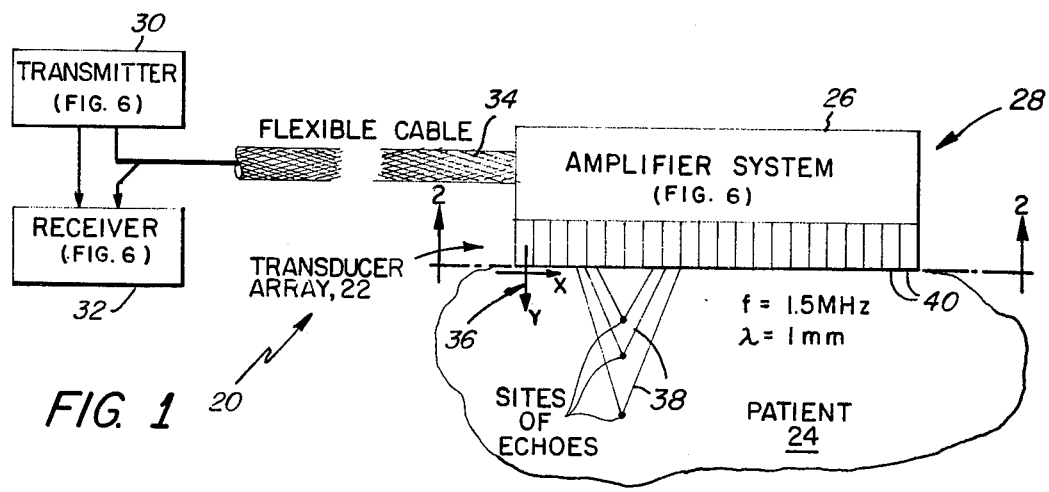
FIG. 1 shows a transducer array of the invention positioned in contact with a subject, such as a portion of a patient in a hospital, the transducer array being coupled to a transmitter and receiver for the transmission of acoustic signals into the subject and the reception of echoes therefrom.

Referring now to FIG. 1, there is seen an imaging system 20 which, in accordance with the invention, comprises a transducer array 22 positioned in contact with a subject 24, and an amplifier system 26. The amplifier system 26 and the transducer array 22 are incorporated within a common module 28. The system 20 further comprises a transmitter 30, a receiver 32 and a flexible cable 34 joining the transmitter 30 and the receiver 32 with the module 28. A coordinate system 36 having X and Y axes is situated at a corner of the module 28 at the surface of the subject 24 for locating sites within the subject 24, the X axis measuring horizontal positions along the interface between the module 28 and the subject 24 while the Y axis measures depth into the subject 24 from the face of the transducer array 22. Also shown are sound rays 38 emanating from sites within the subject 24 to illustrate propagation of echoes from the sites to the transducers of the active portion of the array 22.

As will be seen subsequently, the transmitter 30 transmits a pulse electrical signal via the cable 34 and the amplifier system 26 to the transducer array 22, individual transducers 40 of the array 22 being selectively energized by the pulse signal for transmitting a sonic pulse signal toward the sites in the subject 24. Echo signals propagating from the sites back to the array 22 are coupled via the amplifier system 26 to the receiver 32 which performs a Fresnel multiplication operation and displays the resultant echo. The flexible cable 34 permits the positioning of the module 28 at any desired location on the subject 24.

Figure 2:
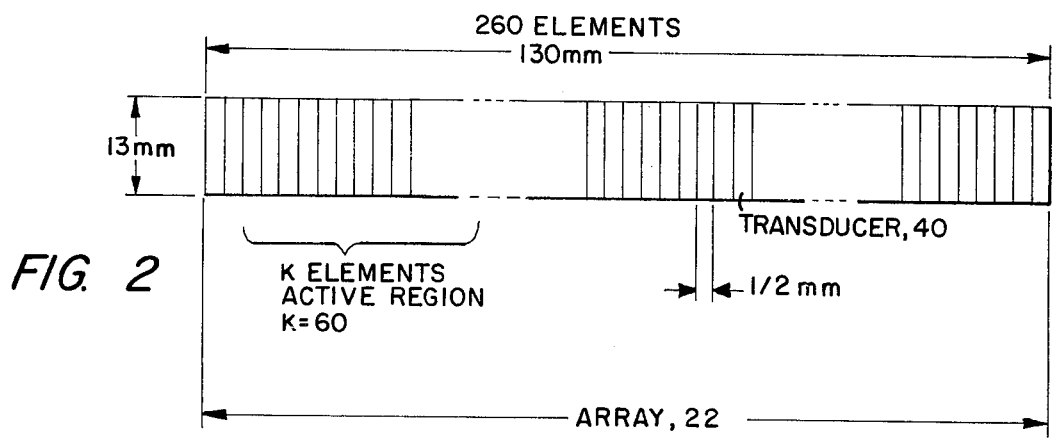
FIG. 2 shows a plan view of the transducer array of FIG. 1 taken along the lines 2—2 of FIG. 1.

Referring also to FIG. 2, the dimensions of an exemplary array 22 are presented. The array is seen to have a width of 13 mm (millimeters), a length of 130 mm, and includes 260 elements, each element being one of the transducers 40 of FIG. 1. As noted in FIG. 1, the frequency of transmission of the sonic energy is given as 1.5 megahertz (MHz) with a wavelength of 1 mm within the subject 24. Each transducer 40 has a front face in the shape of a narrow rectangle wherein the length of each face is 13 mm and the width thereof is $\frac{1}{2}$ mm. Also, by way of example in receiving sonic energy, a group of 60 elements is shown as the active region whereby the Fresnel patterns are formed.

Figure 3:
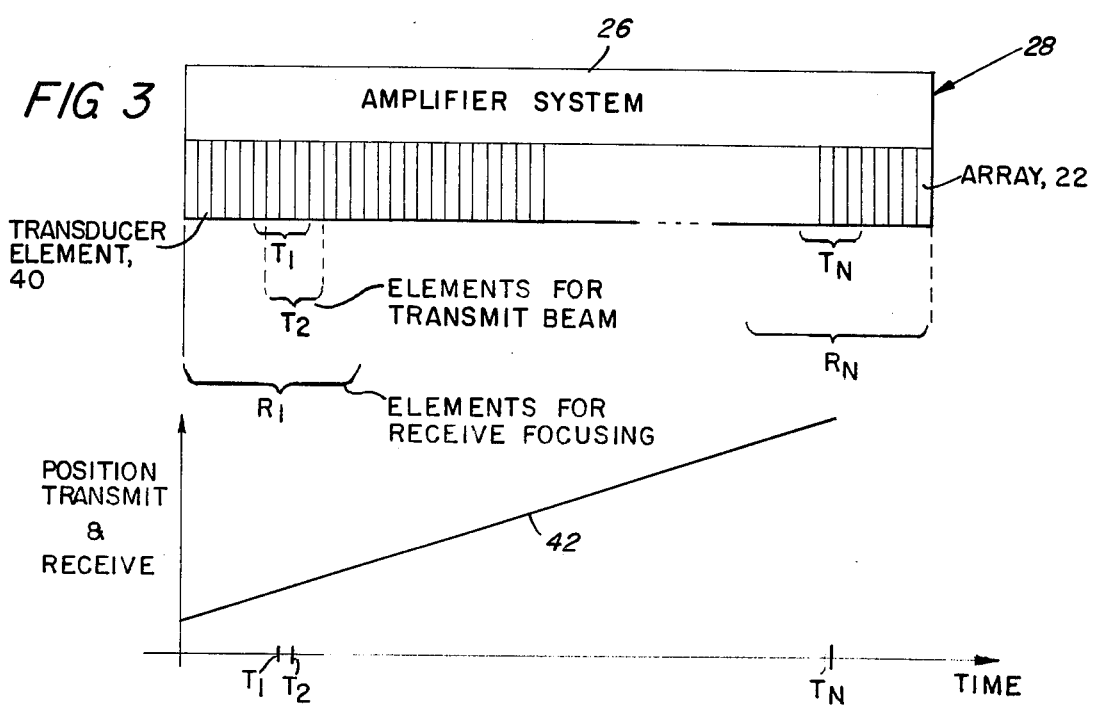
FIG. 3 shows a side view of the transducer array of FIG. 1 in combination with a graph displaying the temporal location of a group of transducers of the array actively participating in the formation of images of sites within the subject of FIG. 1, the graph portraying the side-stepping of the active region for scanning a rectangular swath of the subject.

Referring now to FIG. 3, the group of elements of the array 22 utilized for receiving sonic energy is enclosed by a bracket identified by the legend R while a smaller group of elements utilized for transmitting sonic energy is enclosed by a bracket identified by the legend T. The subscripts 1 and 2 appended after the legends R and T indicate subsequent positions of the group of active elements with the subscript N indicating the final position of the receiving group at the end of a scan along the subject 24 of FIG. 1. The line 42 represents the linear stepping of the group of active elements after each scanning of a group of sites within the subject 24 on a line normal to the center of the groups of active elements. While the line 42 is shown as a straight line, it is to be understood that the actual positions of the centers of the groups of active elements are displaced a step at a time wherein each step may have the width of one transducer 40 or two or more of the transducers 40.

Figure 4:
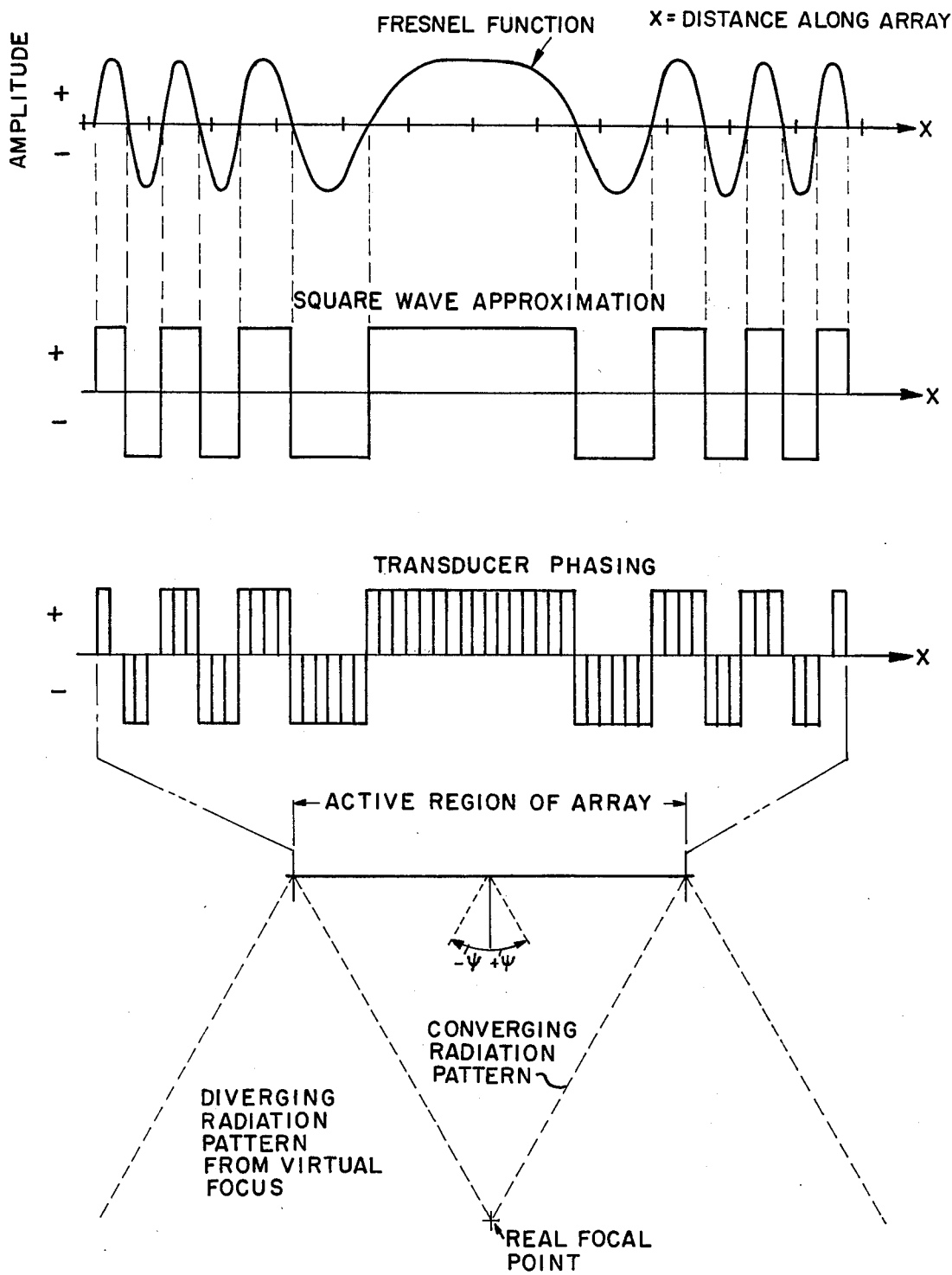
FIG. 4 shows a set of four graphs in registration with each other, the first graph showing a Fresnel function with the horizontal distance along the transducer array of FIG. 1 serving as a parameter thereof, the second graph showing a square wave approximation to the Fresnel function, the third graph showing the multiplication of the signals of individual ones of the transducers of the active region of the array wherein the polarity of the signals subsequent to the multiplication follows the pattern of the square wave approximation of the second graph, and the fourth graph shows the resultant converging radiation pattern, as well as the diverging radiation pattern which is obtained when only one Fresnel function is employed in the signal processing.

Referring now to FIG. 4, the first graphs depicts a Fresnel pattern constructed for a set of elements of the array 22 which comprise the active group of receiving elements. Thus, with reference to FIG. 2, wherein 60 transducers 40 serve as the active elements, the Fresnel pattern of the first graph of FIG. 4 encompasses the 60 elements. Similar comments apply to the second and third graphs which represent a square wave approximation to the Fresnel pattern. Furthermore, with reference to the third graph of FIG. 4, it is noted that the graph shows, by way of example, transducer signal samples that have been multiplied by zero as well as by +1 and −1. Thus, the positive values indicate a multiplication by +1, while the negative values indicate multiplication by the factor −1. It is also noted that the third graph shows a relatively large number of transducer elements of which the signals have a common phase within the central portion of the Fresnel function. Nearer the edges of the Fresnel function, the numbers of transducers involved in any one small band of the Fresnel function is relatively small with only one transducer element being shown for the last band. The multiplying factors utilized in the third graph produce the radiation pattern of the active region portrayed in the fourth graph wherein it is seen that there are two superposed radiation patterns. One of these superposed radiation patterns converges to a real focal point in front of the array 22 of FIG. 1 while the second of the superposed radiation pattern diverges from a virtual focus which would be located behind the array 22 of FIG. 1. In view of the fact that the cosinusoidal Fresnel pattern is an even function of distance along the face of the array 22 while the sinusoidal Fresnel pattern is an odd function of distance along the face of the array 22, the combination of the two patterns result in the removal of the diverging pattern so that, as a result of the signal processing of the invention, only the converging radiation pattern is utilized in forming images of the sites within the subject 24 of FIG. 1.

Figure 5:
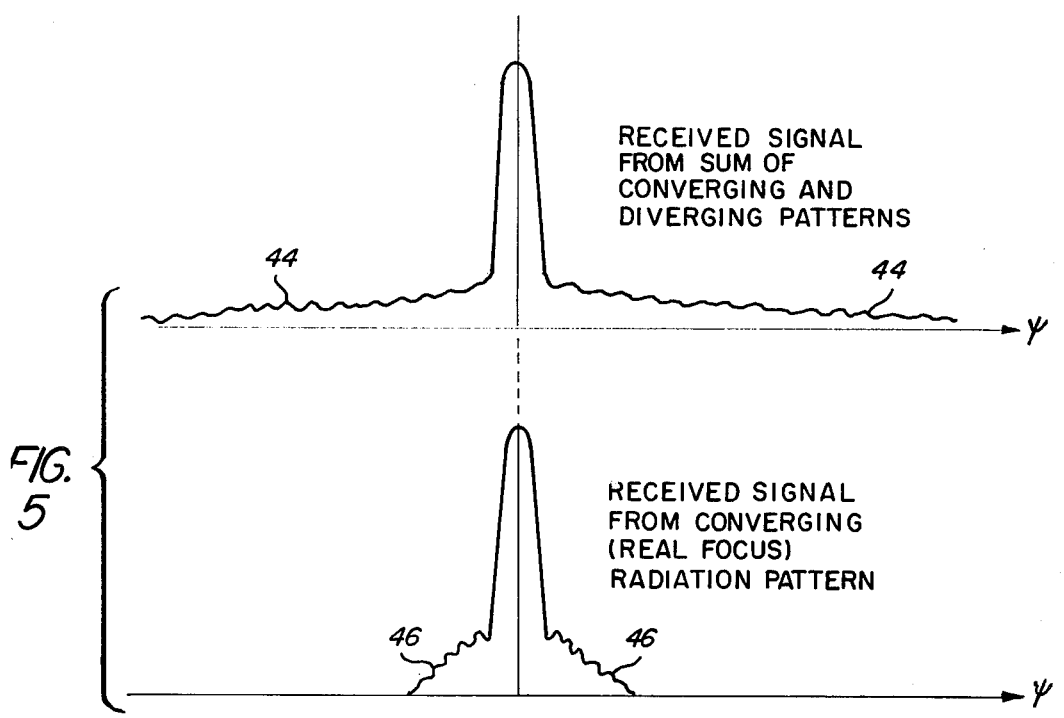
FIG. 5 shows two graphs of the intensity of echo strength from a site within the subject as a function of angle about a normal to the face of the transducer array, the normals and the angles being seen in the fourth graph of FIG. 4, the second graph showing the reduction in noise resulting from the cancellation of signals of the diverging beam in accordance with the invention.

The two graphs of FIG. 5 show the radiation pattern after combination of the signals of the transducers of the array 22 the first graph relating to single one of the aforementioned Fresnel patterns while the second graph relates to the use of both cosinusoidal and sinusoidal Fresnel patterns. The horizontal axis of each graph represents the angle measured relative to a normal to the face of the array, the angles being identified relative to a normal in the fourth graph of FIG. 4. The first graph of FIG. 5 represents the prior art showing substantial noise in the skirts 44 of the radiation pattern. The skirts 46 of the second graph of FIG. 5 show greatly diminished energy content thereby indicating that the signal processing of the invention involving the use of the aforementioned pair of Fresnel patterns has greatly reduced the noise surrounding the desired signals from which the image of the subject 24 is composed. It is also noted that, with the aforementioned use of a Fresnel pattern in nuclear medicine, the imaging in the nuclear medicine case is based on a non-defraction of gamma rays while, in the present case of sonic imaging, defraction and interference phenomena of sonic waves produce the focussing of the radiation pattern upon a focal point in a manner analogous to the Fresnel focussing in optics.

Figure 6:
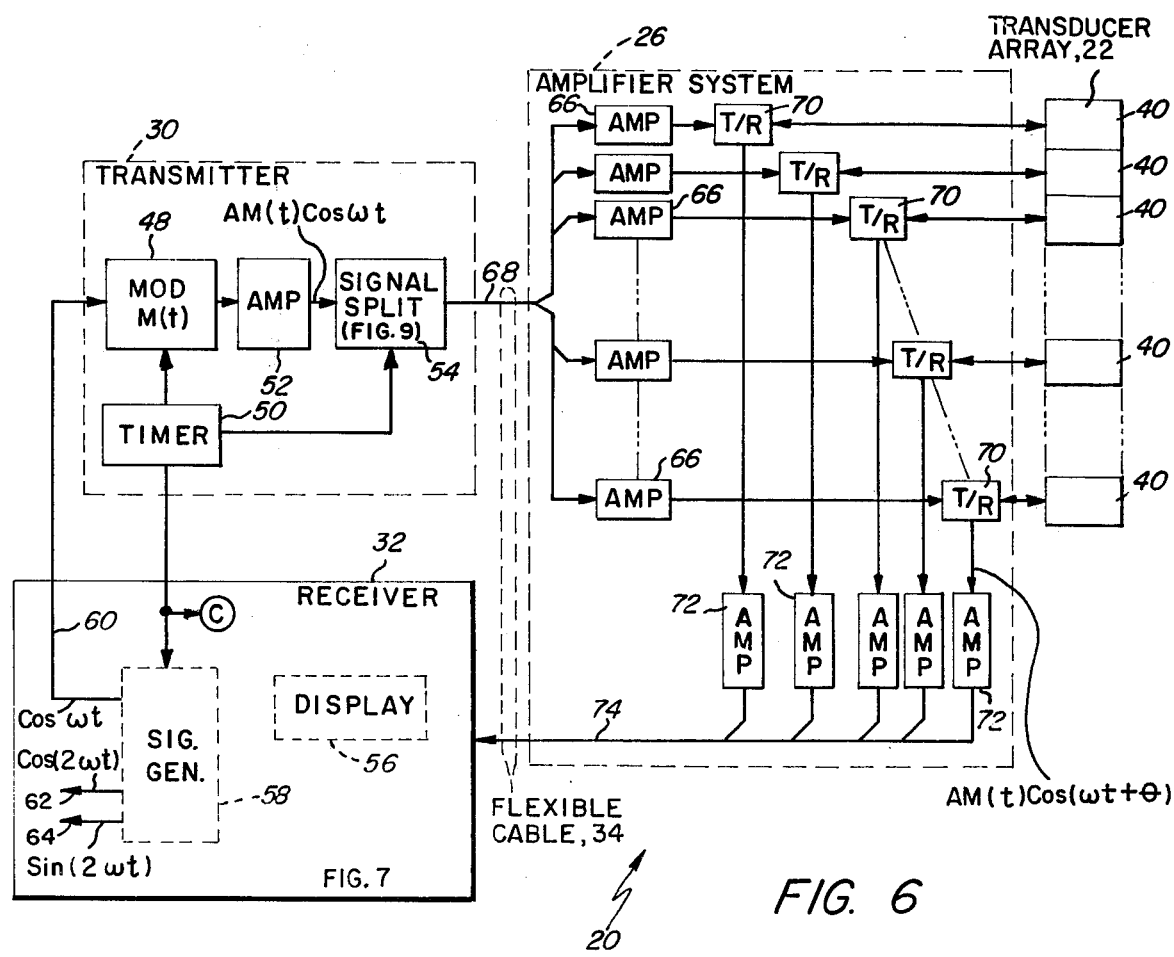
FIG. 6 shows a block diagram disclosing the electrical connections between the transducer array and a transmitter and a receiver of FIG. 1.

Referring now to FIG. 6, the transmitter 30, the receiver 32 and the amplifier system 26 of FIG. 1 are presented in greater detail. The transmitter 30 is seen to comprise a modulator 48, a timer 50, an amplifier 52 and a signal splitter 54. The receiver 32 comprises a display 56 for portraying an image of the subject 24 of FIG. 1 and a signal generator 58 which provides on line 60 the carrier of the signal transmitted by the array 22 as well as a pair of reference signals on lines 62 and 64 which will be utilized, in a manner to be described with reference to FIG. 8, in the processing of signals received by the array 22 for providing the image of the subject 24. The amplifier system 26 comprises a set of amplifiers 66 having their respective input terminals connected by lines seen fanning into line 68 which is coupled to the signal splitter 54, a set of transmit-receive circuits 70 coupled between respective output terminals of the amplifiers 66 and transducers 40 of the array 22, and a set of preamplifiers 72 coupled to respective ones of the circuits 70 for amplifying signals received by respective ones of the transducers 40, the output terminals of respective ones of the preamplifiers 72 being coupled via lines which fan into line 74 for coupling via the cable 34 to the receiver 32.

The operation of the transmitter 30 and the operation of the receiver 32 are synchronized by clock signals provided by the timer 50. In response to the clock signals from the timer 50, the generator 58 applies the aforementioned carrier signal via line 60 to the modulator 48, and the modulator 48 applies an amplitude modulation in the form of a short pulse to the carrier signal. By way of example, the pulse duration provided by the modulator 48 is on the order of 3 microseconds, this being equal to the duration of approximately four cycles of the carrier signal. The amplifier 52 amplifies the power of the pulsed signal of the modulator 48 for driving the signal splitter 54 which will be described with reference to FIG. 9. The two reference signals of the signal generator 58 are at double the frequency of the carrier signal, one of the reference signals having a cosinusoidal waveform and the other reference signal having a sinusoidal waveform. The signal splitter 54 selects a group of transducers 40, corresponding to the transmitting group of FIG. 3, and distributes the pulsed carrier signal from the amplifier 52 via a set of conductors represented by line 68 in the cable 34 to the respective ones of the amplifiers 66. The amplifiers 66 provide sufficient power to the pulsed carrier signals for driving the transducers 40 for ensonifying the subject 24 of FIG. 1. The circuits 70 couple the transmitted signal from the respective amplifiers 66 to the transducers 40 while isolating the signals from the preamplifiers 72. The signals received by the transducers 40 are coupled via the circuits 70 and the preamplifiers 72 to the receiver 32.

Figure 7:
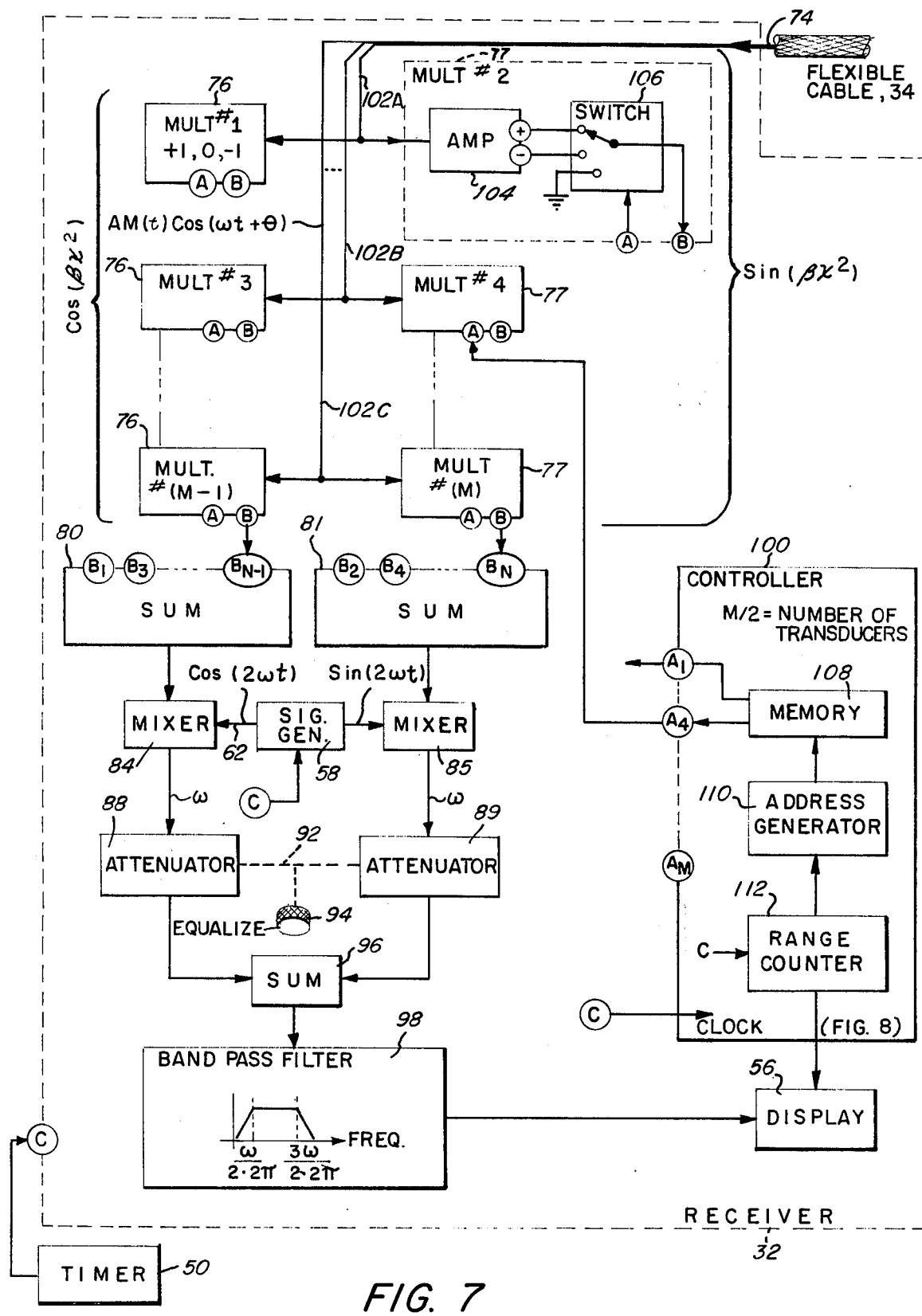
FIG. 7 is a block diagram of the receiver of FIGS. 1 and 6 disclosing the multiplication of the transducer signals to provide the pair of Fresnel patterns.

Referring now to FIG. 7, there is seen a detailed block diagram of the receiver 32 of FIGS. 1 and 6. Line 74 of the cable 34 is seen to be coupled to the receiver 32 as well as clock signals at terminal C from the timer 50 as was noted hereinabove with reference to FIG. 6. The receiver 32 comprises a first set of multipliers 76, a second set of multipliers 77, summers 80 and 81, mixers 84 and 85, attenuators 88 and 89 which are mechanically coupled via line 92 to a knob 94, a summer 96, a bandpass filter 98, a controller 100, and the display 56 and the signal generator 58 which were previously seen in FIG. 6. Individual lines 102A–C which fan out from the cable represented by the line 74, each carry the signal of one of the transducers 40 of FIG. 6, and each is coupled to a pair of multipliers 76 and 77. For example, the line 102A is coupled to multiplier #1 and multiplier #2. The line 102B is coupled to the multiplier #3 and the multiplier #4. There are a total of M multipliers 76–77 where M is equal to twice the number of transducers 40.

The set of multipliers 76, this comprising the odd numbered multipliers, provides multiplication by the set of factors corresponding to the cosinusoidal Fresnel pattern and will be sometimes referred to hereinafter as the cosine branch. The set of multipliers 77, this being the even numbered multipliers, provides multiplication by the set of factors corresponding to the sinusoidal Fresnel pattern and will be sometimes referred to hereinafter as the sine branch. Thus, the signal from each transducer is applied to one multiplier of each set. Thereby, each transducer 40 of the active region for receiving radiation, as disclosed in FIG. 3, provides a contribution to the generation of the cosinusoidal Fresnel pattern and the sinusoidal Fresnel pattern. The product of each of the multipliers 76–77 appears at terminal B, the input terminals of the summers 80–81 being similarly labeled with the legend B but being further identified by the numerals corresponding to the individual ones of the multipliers 76–77. Thus, terminal B of multiplier #1 is connected to terminal B1 of the summer 80, with similar connections being applied to the other multipliers such as the connection of terminal B of the multiplier #4 to terminal B4 of the summer 81. In this way, the products of each of the odd numbered multipliers 76 are summed together by the summer 80, and the products of each of the even numbered multipliers 77 are summed together by the summer 81.

Figure 8:
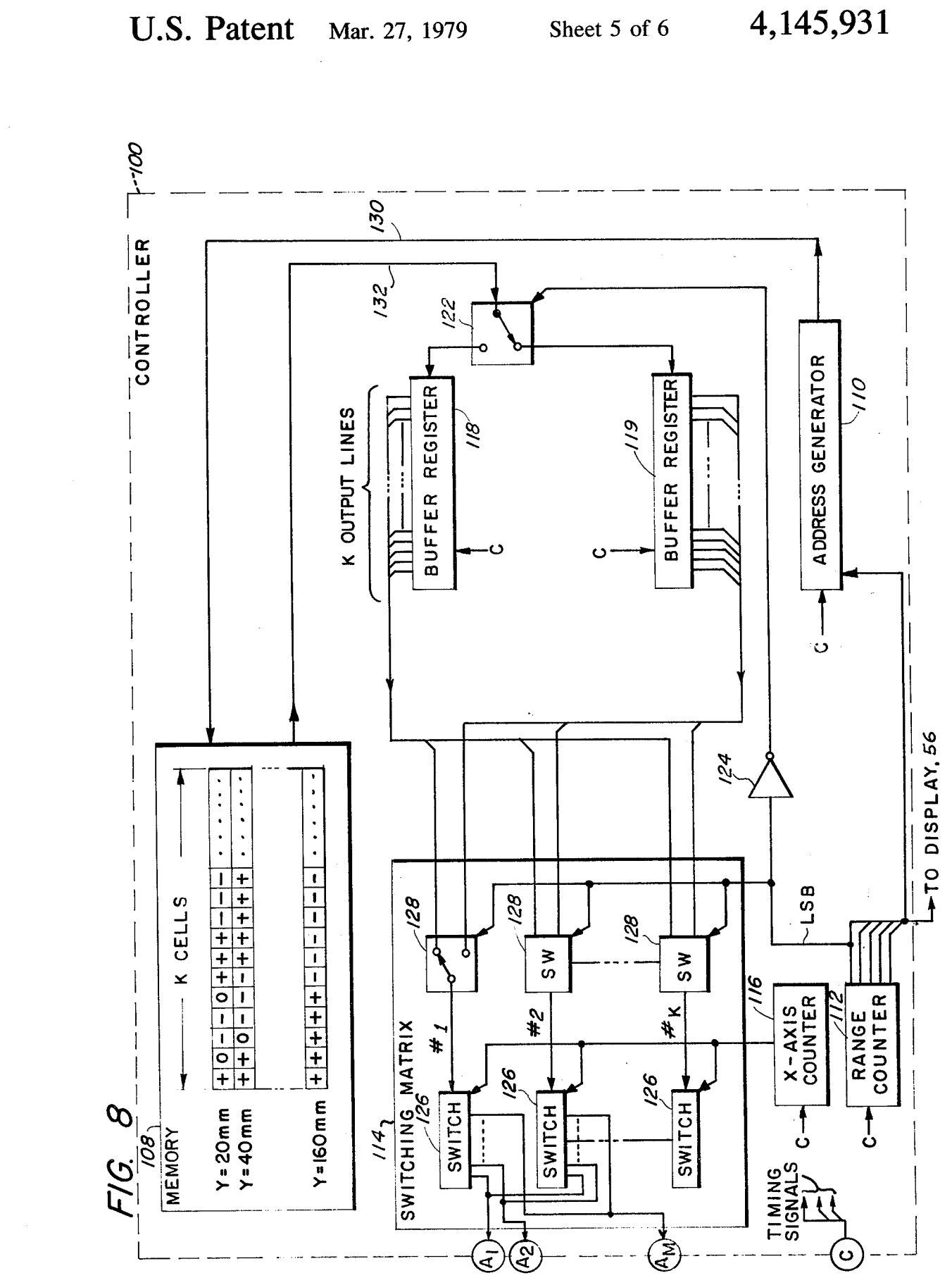

Each of the multipliers 76–77 provides multiplication by a factor of $+1$, $-1$ or 0 as is shown in the block representing the multiplier #1. Each of the multipliers is comprised of an amplifier 104 and a switch 106 as is shown in the block representing the multiplier #2. The amplifier 104 provides positive and negative polarities of the signal at its input terminal, such as a signal on line 102A, the signals of positive and negative polarity being coupled to two input terminals of the switch 106. A third input terminal of the switch 106 is grounded. Terminal B of the multipliers 76–77 is selectively coupled by the switch 106 to one of the input terminals of the switch 106 whereby the product appearing at terminal B includes one of the afore-mentioned multiplying factors. The switch 106 in each of the multipliers 76–77 is controlled via a signal, such as a two-bit digital signal, at terminal A. The signals coupled to the terminals A in each of the multipliers 76–77 are provided by the controller 100 which is seen to have a set of output terminals identified by the legend A, the identification of the output terminals further including the numerals 1-M to identify the specific one of the multipliers 76–77 to which the switch control signal is being applied. The controller 100 is described briefly in FIG. 7 and in greater detail in FIG. 8, FIG. 7 showing a memory 108, an address generator 110 and a range counter 112. In accordance with the range or depth of a site within the subject 24 of FIG. 1, the counter 112 counting the range of the site, the generator 110 addresses the memory 108 to provide the set of multiplying factors for a Fresnel pattern focussed at that site.

The sum produced by the summer 80 is multiplied in the mixer 84 by the cosinusoidal reference of the generator 58, the mixer providing the difference between the reference frequency and the transmitted frequency in the output product. The mixer 85 operates in the same fashion as does the mixer 84 to provide the product of the sum of the summer 81 and the sinusoidal reference signal. As was mentioned earlier with reference to FIG. 6, the cosinusoidal reference on line 62 and the sinusoidal reference on line 64 are both at double the frequency of the carrier from the transmitted signal. The amplitudes of the products of the mixers 84 and 85 are equalized by the attenuators 88 and 89, the attenuators 88–89 being operated by the knob 94 for varying the attenuation of the product of the mixer 84 relative to that of the mixer 85 to produce the desired equalization. Thereupon, the attenuated signals as provided by the attenuators 88–89 are summed together by the summer 96 and coupled via the filter 98 to the display 56. The filter 98 has a pass band sufficiently wide to pass the sum signal of the summer 96 while attenuating harmonics thereof resulting from the action of the mixers 84–85. A graph within the block representing the filter 98 shows exemplary cut-off frequencies at ½ and 3/2 of the transmitted frequency. The signal produced by the filter 98 represents the image of one of the sites in the subject 24 of FIG. 1 as is produced by the converging radiation pattern of FIG. 4, the diverging radiation pattern having been canceled out in the summer 96. The range counter 112 is coupled to the display 56 to provide a display of images of the sites by the filter 98 as a function of range provided by the counter 112.

Referring now to FIG. 8, the controller 100 is seen to comprise the memory 108, the address generator 110 and the range counter 112 which was previously seen in FIG. 7. In addition, the controller 100 comprises a switching matrix 114, a counter 116, buffer storage registers 118–119, a switch 122 and a digital inverter 124. The switching matrix 114 comprises a set of switches 126 and a set of switches 128. As noted hereinabove with reference to FIG. 7, the memory 108 stores sets of factors, these factors being presented graphically in FIG. 8 in a diagrammatic representation of the storage wherein individual rows correspond to depth of site as measured in the Y direction of the coordinate system 36 in FIG. 1. Thus, by way of example, a row corresponds to Y = 20 mm, Y = 40 mm with further rows corresponding to increments of 20 mm until the last row shown as Y = 160 mm. Each row stores the factors for both the cosinusoidal Fresnel pattern and the sinusoidal Fresnel pattern, this corresponding to the odd numbered multipliers 76 and the even numbered multipliers 77 of FIG. 7. An address for addressing individual cells of the memory 108 is provided on line 130 from the generator 110. The stored data of the memory 108 is read-out on line 132 in response to the address on line 130, the stored data on line 132 being coupled by the switch 122 alternately to the register 118 and the register 119. As seen in FIG. 2, the number of active elements in the region of the array 22 used for forming the Fresnel focussing is represented by the letter K. In the example described with reference to the FIGS. 2 and 4, K is assumed equal to 60. Accordingly, instead of storing pairs of factors for all 260 elements of the array 22 of FIG. 2, the memory 108 stores pairs of factors for each of the 60 elements of the active region, this totaling 120 factors for each value of Y. Accordingly, each row of the memory 108 of FIG. 8 has 120 cells for storing the 60 factors of the cosinusoidal Fresnel pattern and the 60 factors of the sinusoidal Fresnel pattern. The desired factors are read out serially on line 132 but utilized simultaneously by the multipliers 76–77 of FIG. 7. The registers 118–119 provide buffer storage of these factors to permit both the serial read-out on line 132 and the simultaneous control of multiplication by signals at the terminals A1–AM.

The coupling of the factors from the line 132 to the terminals A of the controller 100 is accomplished as follows. The switches 128 select alternately data stored in the registers 118–119. The switches 128 are coupled to the same one of the registers 118–119. Thus, as seen in FIG. 8, a switch 128 is seen coupling signals from the register 118 and, accordingly, the switch 122 is seen coupling signals into the register 119. In this way, signals are read-out from the register 118 in parallel via the K output lines to respective ones of the switches 128 while the register 119 is being filled with new values of data stored in the memory 108. The output signals of the switches 128, shown on lines #1, #2 and #K are applied to respective ones of the switches 126. Each switch 126 is in the form of a multiple selector switch or multiplexer and has a set of output terminals equal in number to the number of terminals A. Thereby, in response to a digital signal from the counter 116, each switch 126 couples the signal from its input terminal to one of the terminals A1–AM.

The operation of the switches 126 may be further explained by way of example. In response to clock pulses provided by the timer 50 at terminal C, the counter 116 counts successive range scans of a set of sites within the subject 24 such as the three sites shown in FIG. 1. Upon completion of each range scan, a clock pulse is applied to the input terminal of the counter 116, whereupon the counter advances its count to indicate the next position along the X axis of FIG. 1 for the next range scan along the Y axis of FIG. 1. The coupling of the switches 126 to the terminals A1–AM is accomplished in a manner whereby, in response to a digital signal representing a count of one from the counter 116, the first of the switches 126 couples the signal from line #1 to terminal A1, the second of the switches 126 couples the signal from line #2 to terminal A2, and similarly with the remaining ones of the K switches 126. In this way, the counter 116 in conjunction with the switches 126 accomplishes the side-stepping of the range scans along the X axis of FIG. 1 to produce the image in the form of a swath along the X axis of the subject 24.

The range counter 112, in response to clock pulses provided by the timer 50 by the terminal C, counts individual increments of range or depth along the Y axis of FIG. 1. The least significant bit drives the switches 128 and the switch 122 to accomplish the aforementioned alternation in the use of the registers 118 and 119. The logic state of the least significant bit changes state with each increment in range, these changes in state operating the switches 128 to accomplish the aforementioned switching between the registers 118–119. The least significant bit from the range counter 112 is coupled via the inverter 124 to the switch 122, the inverter 124 complementing the logic state so that the switch 122 is directed toward the register 119 while the switches 128 are directed to the register 118. Clocking of data through the registers 118–119 is accomplished by clock pulse signals from the timer 50 which are coupled via terminal C.

Figure 9:
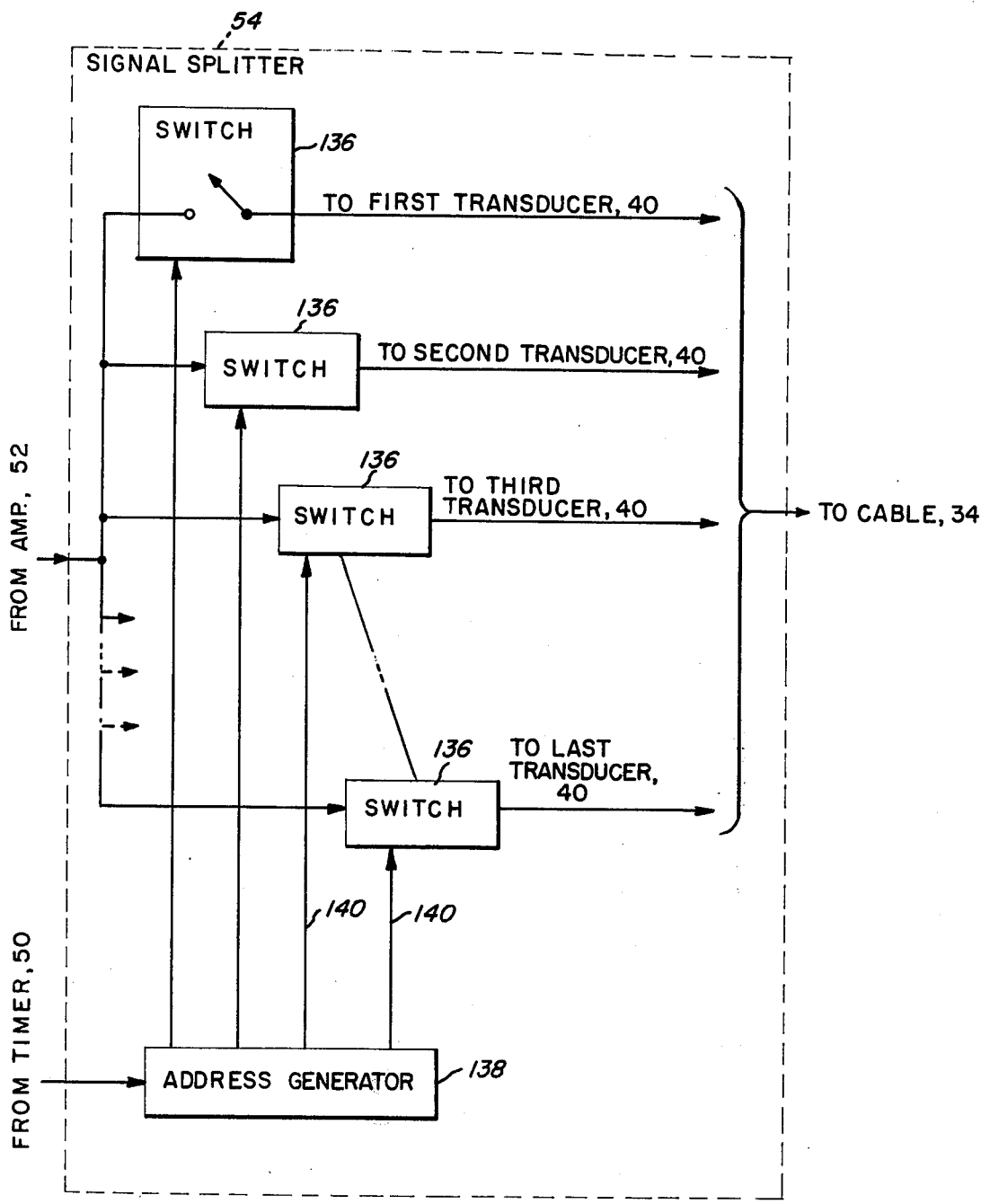
FIG. 9 is a block diagram of a signal splitter in the transmitter of FIG. 6.

Referring now to FIG. 9, the signal splitter 54 of FIG. 6 is seen to comprise a set of switches 136 coupled to respective ones of the transducers 40, and an address generator 138 coupled via lines 140 to individual ones of the switches 136. The generator 138, in response to the clock pulse signals from the timer 50, addresses individual ones of the switches, via the lines 140, to couple the signal from the amplifier 52 to the respective ones of the transducers 40. A group of four switches is addressed to energize the exemplary group of four transducers 40, shown in FIG. 3, for transmitting a beam of sonic energy. Groups of the switches 136 are addressed sequentially corresponding to the side-stepping of the group of transducers 40 of FIG. 3 for scanning the beam along the X coordinate of the coordinate system 36 of FIG. 1.

MATHEMATICAL DESCRIPTION

The foregoing system can be further described mathematically as follows. The signal received by one of the transducers, $s(t,x)$, is given by $$s(t,x) = A(x) \cos(\omega t + \beta \phi_x) \tag{1}$$

where
x is distance along the array,
t is time,
$\phi_x$ is a phase angle dependent on the x coordinate,
$\omega$ is radian frequency and
$A(x)$ is amplitude dependent on the x coordinate.

The expression for the signal $s_c(t,x)$, passing through the cosine branch of FIG. 7 and appearing at the output of the mixer 84, assuming the true Fresnel pattern shown in the first graph of FIG. 4 rather than the square wave approximation shown in the second graph of FIG. 4, is given by $$s_c(t,x) = K_c A(x) \cos(\omega t + \phi_x) \cos(\beta x^2) \cos(2\omega t) \tag{2}$$

After dropping the high frequency term $(3\omega)$ which would be filtered out by the electrical circuitry, the baseband component $s_{cb}(t,x)$, is given by $$\begin{aligned}s_{cb}(t,x) &= (K_c/2)A(x)\cos(\omega t - \phi_x)\cos(\beta x^2) = \\ &(K_c/4)A(x)\cos(\omega t - \phi_x + \beta x^2) + (K_c/4)A(x) \\ &\cos(\omega t - \phi_x - \beta x^2)\end{aligned} \tag{3}$$

where $K_c$ is an amplitude scale factor and $\beta$ is a constant in the Fresnel term. The corresponding signals of the sine branch $s_s(t,x)$ and $s_{sb}(t,x)$, appearing at the output of the mixer 85 are given by $$s_s(t,x) = K_s A(x) \cos(\omega t + \phi_x) \sin(\beta x^2) \sin(2\omega t) \tag{4}$$

$$\begin{aligned}s_{sb}(t,x) &= (K_s/2)A(x)\sin(\omega t - \phi_x)\sin(\beta x^2) = \\ &(K_s/4)A(x)\cos(\omega t - \phi_x - \beta x^2) - (K_s/4)A(x) \\ &\cos(\omega t - \phi_x + \beta x^2)\end{aligned} \tag{5}$$

where $K_s$ is an amplitude scale factor.

Upon adjusting the attenuators 88 and 89 to equalize the amplitudes $K_c A(x)$ and $K_s A(x)$ of the signals of the cosine and sine branches, the sum of the signals of the cosine and sine branches, $v_{out}(t,x)$, appearing at the output of the summer 96 is given by the sum of Equations (3) and (5), namely, $$v_{out}(t,x) = KA(x) \cos(\omega t - \phi_x - \beta x^2) \tag{6}$$

The expression of Equation (6) contains only one term with $\beta x^2$ while an extra term in $\beta x^2$ appears in both Equations (3) and (5). It is these extra terms which produce the undesired diverging beam of the prior art. When $\beta$ is adjusted so that $\phi_x = -\beta x^2$, the transducers are focussed on a wave with curvature about the desired focal point. The above analysis describes receiver operation; for a transmitter (not shown in the figures) the mathematical analysis is similar.

This system can be made to dynamically focus, that is, the focal length of the transducer array can be changed, as noted hereinabove, as a function of time to track the return echoes. This is accomplished by changing the switches 106 of FIG. 7 in time so the quadratic term $\beta x^2$ matches the curvature of the returning echoes.

It is understood that the above-described embodiments of the invention are illustrative only and that modifications thereof my occur to those skilled in the art. Accordingly, it is desired that this invention is not be limited to the embodiments disclosed therein but is to be limited only as defined by the appended claims.

What is claimed is:

1. An imaging system comprising:
   an array of radiating elements oriented toward a subject for receiving radiant energy from sites within said subject;
   first and second means coupled to each of said elements for selecting polarities of signals produced by said elements in response to said radiant energy;
   means coupled to said first and said second selecting means to operate said first and said second selecting means in accordance with the locations of said elements in said array to provide patterns of said polarity, said first selecting means providing a cosinusoidal Fresnel pattern of polarity, and said second selecting means providing a sinusoidal Fresnel pattern of polarity;
   first and second means for summing signals coupled respectively by said first and said second selecting means;
   means coupled to said summing means for multiplying sums of said first and said second summing means respectively by cosinusoidal and sinusoidal reference signals to provide respectively first and second products;

means coupled to said multiplying means for equalizing the amplitudes of said products of said multiplying means; and third summing means coupled to said equalizing means for summing said products to produce a radiation pattern focussed on one of said sites.

2. An imaging system comprising:

an array of radiating elements;

first means for modulating signals coupled to said radiating elements according to a cosinusoidal Fresnel pattern;

second means for modulating signals coupled to said radiating elements according to a sinusoidal Fresnel pattern; and means coupled to said first and second modulating means for combining signals modulated with said cosinusoidal Fresnel pattern and signals modulated with said sinusoidal Fresnel pattern to produce an image of a subject viewed by said array of radiating elements.

* * * * *